(12) United States Patent
Akagane et al.

(10) Patent No.: US 11,426,227 B2
(45) Date of Patent: Aug. 30, 2022

(54) TREATMENT TOOL

(71) Applicant: Olympus Corporation, Hachioji (JP)

(72) Inventors: Tsunetaka Akagane, Hachioji (JP);
Yoshitaka Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 347 days.

(21) Appl. No.: 16/600,401

(22) Filed: Oct. 11, 2019

(65) Prior Publication Data
US 2020/0038092 A1 Feb. 6, 2020

Related U.S. Application Data

(63) Continuation of application No. PCT/JP2017/015439, filed on Apr. 17, 2017.

(51) Int. Cl.
*A61B 18/08* (2006.01)
*A61B 18/00* (2006.01)

(52) U.S. Cl.
CPC .... *A61B 18/085* (2013.01); *A61B 2018/0063* (2013.01); *A61B 2018/00095* (2013.01);
(Continued)

(58) Field of Classification Search
CPC .. A61N 1/18; A61B 1/00002; A61B 1/00131; A61B 1/00147; A61B 17/00;
(Continued)

(56) References Cited

U.S. PATENT DOCUMENTS 5,308,311 A 5/1994 Shaw
2002/0099369 A1* 7/2002 Schulze ............. A61B 18/1445
606/50
(Continued)

FOREIGN PATENT DOCUMENTS

JP U52107761 3/1979
JP 7-509620 10/1995
(Continued)

OTHER PUBLICATIONS

International Search Report and Written Opinion from corresponding International Application No. PCT/JP2017/001544, dated Apr. 18, 2017.

*Primary Examiner* — Linda C Dvorak
*Assistant Examiner* — Mystee Nguyen Delgado
(74) *Attorney, Agent, or Firm* — Oliff PLC

(57) ABSTRACT

The disclosed technology is directed to a treatment tool having a blade configured to engage with a treatment target. A heater is configured to be spaced apart from the blade. A first thermally conductive member is sandwiched between the blade and the heater so as to transmit heat to the blade. The first thermally conductive member includes respective first and second portions each of which is disposed on respective distal-end and proximal-end sides in longitudinal directions of the blade for thermally conducting a different prescribed quantity of heat per unit time from each of the respective first and second portions to the blade via the heater. The first thermally conductive member includes a first thermal conductivity anisotropy that is higher in longitudinal directions of the blade and is lower in widthwise directions transverse to the longitudinal directions.

12 Claims, 10 Drawing Sheets

(52) U.S. Cl.
CPC .............. *A61B 2018/00601* (2013.01); *A61B 2018/00607* (2013.01)

(58) Field of Classification Search
CPC .............. A61B 18/00; A61B 2218/00; A61B 17/00234; A61B 18/085; A61B 2018/00095; A61B 2018/00601; A61B 2018/00607; A61B 2018/0063; A61B 17/3201; A61B 17/3209; A61B 17/3205; A61B 17/32; A61B 2018/00005; A61B 18/08; A61B 2018/00589; A61B 2090/034; A61B 2018/1452; A61B 18/12; A61B 18/1442; A61B 2018/1405; A61B 2018/1497; A61B 18/1445; A61B 2018/00089; A61B 2018/00071; A61B 2018/00577; A61B 2018/00595; A61B 2018/00613; A61B 18/1206; A61B 18/14; A61B 17/28
See application file for complete search history.

(56) References Cited

U.S. PATENT DOCUMENTS

| | | | |
|---|---|---|---|
| 2003/0187429 A1* | 10/2003 | Karasawa | A61B 18/085 606/29 |
| 2003/0195513 A1* | 10/2003 | Truckai | A61B 18/1442 606/51 |
| 2011/0014417 A1* | 1/2011 | Lemak | H01L 23/4006 427/407.1 |
| 2014/0155877 A1 | 6/2014 | Yasunaga | |
| 2016/0074095 A1* | 3/2016 | Strobl | A61B 18/1445 606/51 |
| 2017/0042602 A1 | 2/2017 | Takashino et al. | |
| 2017/0245923 A1* | 8/2017 | Takashi | A61B 18/085 |
| 2017/0323780 A1* | 11/2017 | Koga | B32B 9/041 |

FOREIGN PATENT DOCUMENTS

| | | |
|---|---|---|
| JP | 2003225246 | 8/2003 |
| JP | 2016-027843 | 2/2016 |
| JP | 2016-110757 | 6/2016 |
| WO | 2016067950 | 5/2016 |

* cited by examiner

TREATMENT TOOL

CROSS-REFERENCE TO RELATED APPLICATION

This application is a continuation application of PCT Application No. PCT/JP 2017/015439 filed on Apr. 17, 2017, which is hereby incorporated by reference in its entirety.

TECHNICAL FIELD

The disclosed technology relates to a treatment tool for treating a treatment target such as, for example, a biological tissue or also known as a biotissue with thermal energy.

DESCRIPTION OF THE RELATED ART

Japanese Patent Application JP 2013-34568A discloses a general therapeutic treatment apparatus. The therapeutic treatment apparatus calculates the temperature of a heat generating tip based on the resistance value of the heat generating tip. The temperature of a sheet heater can be controlled based on the value of electric power applied to the heat generating tip without determining the temperature of the sheet heater.

BRIEF SUMMARY OF EMBODIMENTS

The disclosed technology has been made in view of the foregoing.

One aspect of the disclosed technology is directed to a treatment tool having a blade configured to engage with a treatment target. A heater is configured to be spaced apart from the blade. A first thermally conductive member is sandwiched between the blade and the heater so as to transmit heat to the blade. The first thermally conductive member includes a first thermal conductivity anisotropy that is higher in longitudinal directions of the blade and is lower in widthwise directions transverse to the longitudinal directions.

Another aspect of the disclosed technology is directed to a treatment tool having a blade configured to engage with a treatment target. A heater is configured to be spaced apart from the blade. A first thermally conductive member is sandwiched between the blade and the heater so as to transmit heat to the blade. The first thermally conductive member includes respective first and second portions each of which disposed on respective distal-end and proximal-end sides in longitudinal directions of the blade for thermally conducting a different prescribed quantity of heat per unit time from each of the respective first and second portions to the blade via the heater.

A further aspect of the disclosed technology is directed to a treatment tool having a blade configured to engage with a treatment target. A heater is configured to be spaced apart from the blade. A first thermally conductive member is sandwiched between the blade and the heater so as to transmit heat to the blade. The first thermally conductive member includes respective first and second portions each of which is disposed on respective distal-end and proximal-end sides in longitudinal directions of the blade for thermally conducting a different prescribed quantity of heat per unit time from each of the respective first and second portions to the blade via the heater. The first thermally conductive member includes a first thermal conductivity anisotropy that is higher in longitudinal directions of the blade and is lower in widthwise directions transverse to the longitudinal directions.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

In a case where a heat generating body such as a heater is used in a treatment tool, the heat generating body may suffer temperature variations therein. The treatment tool may then be unable to achieve a stable treatment result where a temperature variation occurs in the heat generating body. There have been demands for a treatment tool whose temperature variations have been corrected. There are occasions in which a biotissue is cut off by a portion of a proximal-end side or distal-end side of a heat generating body that is shaped as a rod. However, when a biotissue is cut off with a portion of the heat generating body, the other portion of the heat generating body that is not in contact with the biotissue produces idle heat and tends to be overheated. The overheated heat generating body is likely to deteriorate sooner. Therefore, there have also been demands for a treatment tool that is prevented from being overheated. Consequently, there have been demands for a treatment tool that is capable of freely controlling a distribution of heat on a treatment portion of the treatment tool depending on a treatment target to be treated accordingly.

It is an object of the disclosed technology to provide a treatment tool that is capable of freely controlling a distribution of heat.

First Embodiment

A treatment tool according to a first embodiment will be described hereinafter with reference to FIGS. 1 through 3.

Figure 1:
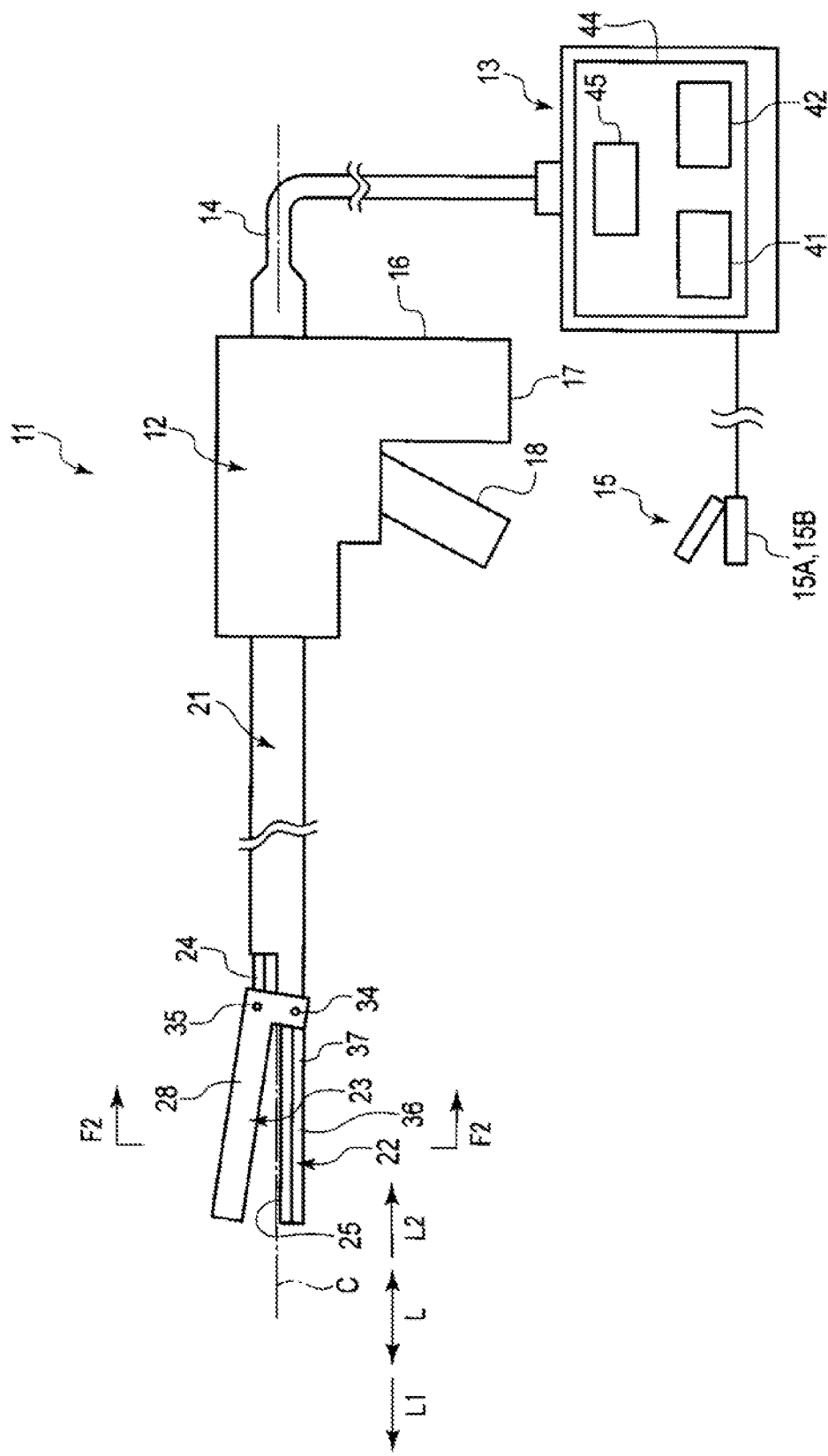
FIG. 1 is a schematic view illustrating the overall makeup of a treatment tool according to a first embodiment.

As illustrated in FIG. 1, a treatment tool 11, i.e., a medical device or a thermal treatment tool, includes a hand piece 12, a power supply unit 13, a cable 14 interconnecting the hand piece 12 and the power supply unit 13, and a foot switch 15, i.e., a switch, connected to the power supply unit 13 for selectively turning on and off the energy output from the power supply unit 13.

Figure 2:
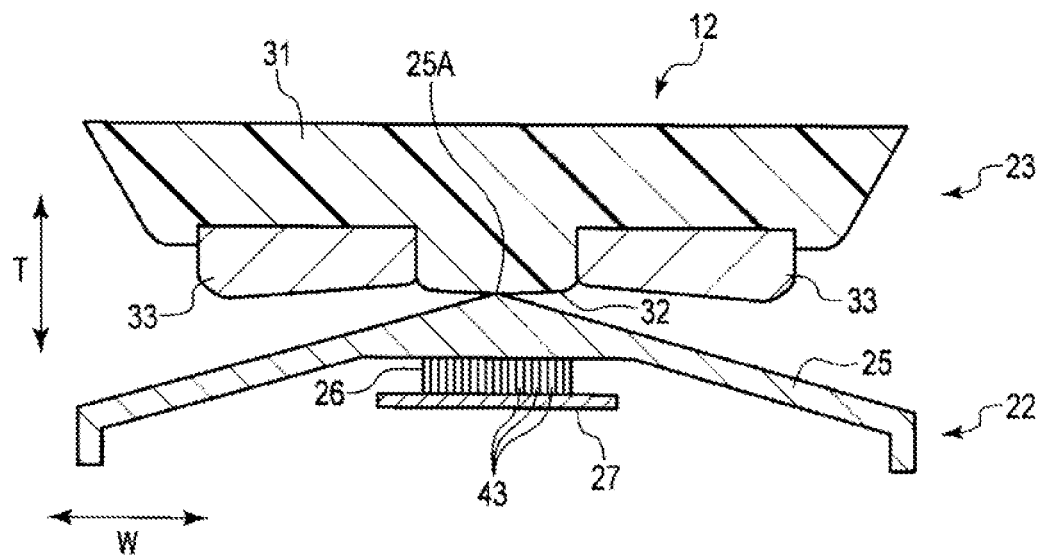
FIG. 2 is a cross-sectional view taken along line F2-F2 of FIG. 1.
Figure 3:
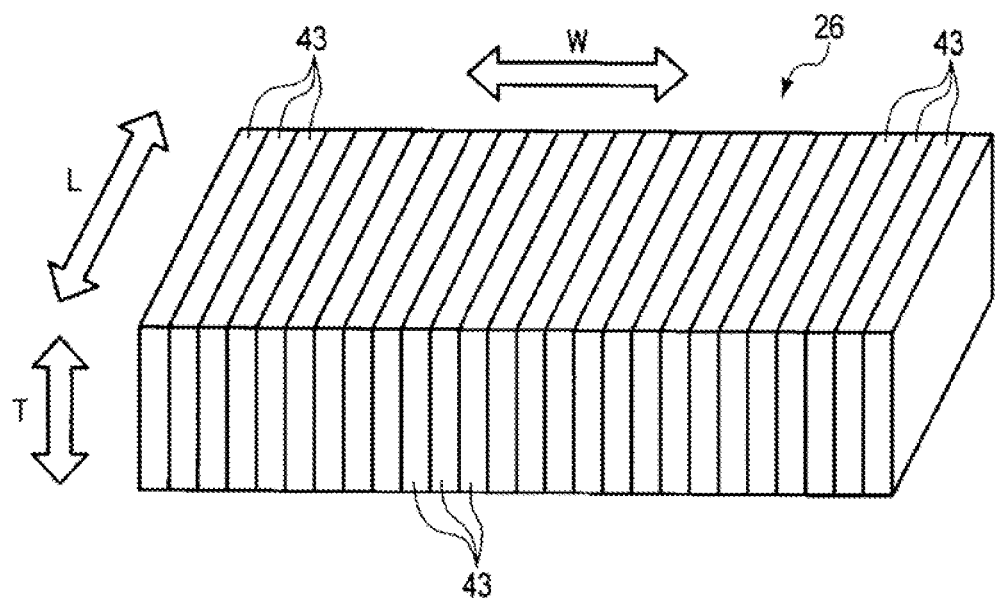
FIG. 3 is a perspective view of a thermally conductive member illustrated in FIG. 2.

As illustrated in FIGS. 1 through 3, the hand piece 12 includes a case 16 as an outer shell, a fixed handle 17 attachably disposed on the case 16, a movable handle 18 angularly movable with respect to the case 16, a tubular portion 21, i.e., an outer sheath, rotatably mounted on the case 16, a rod-shaped treatment portion 22 disposed on a distal-end side of the tubular portion 21, a rod-shaped second treatment portion 23 disposed on the distal-end side of the tubular portion 21 for engagement with and disengagement from the treatment portion 22, and a second tubular portion 24, i.e., an inner sheath, disposed in the tubular portion 21 and movable back and forth for angularly moving the second treatment portion 23. According to the present embodiment, one of two directions parallel to longitudinal directions L of a blade 25 is referred to as a distal-end direction LA, and the direction opposite the distal-end direction as a proximal-end direction L2. The tubular portion 21 has a central axis C. The longitudinal directions L of the blade 25 extend along the central axis C of the tubular portion 21. Directions transverse to the longitudinal directions L of the blade 25 are referred to as widthwise directions W of the blade 25. Directions extending across the blade 25, a thermally conductive member 26, and a heater 27 are referred to as thicknesswise directions T of the blade 25. The directions and axis thus defined will be referred to in the following description.

The surgeon operates the foot switch 15 to turn on and off the energy, i.e., thermal energy and high-frequency current energy, applied to a biotissue as a treatment target. The foot switch 15 may include a first switch 15A and a second switch 15B. The first switch 15A corresponds to a coagulation mode, for example, and outputs only high-frequency energy suitable for coagulating a biotissue and sealing a blood vessel, for example. The second switch 15B corresponds to a coagulation and incising mode, for example, and outputs thermal energy and high-frequency energy suitable for coagulating and incising a biotissue or sealing and incising a blood vessel, for example.

As illustrated in FIGS. 1 and 2, the second treatment portion 23 has a second treatment portion body 28 made of a metal material or the like, for example, and substantially shaped as a beak, an electrode support 31 mounted on the second treatment portion body 28, an abutment portion 32 disposed on a portion of the electrode support 31, and a pair of electrodes 33 disposed one on each side of the abutment portion 32. The second treatment portion body 28 serves as an outer shell of the second treatment portion 23 and covers the side of the second treatment portion 23 that is opposite its side facing the treatment portion 22. The electrode support 31 and the abutment portion 32 are made of a synthetic resin material, e.g., polytetrafluoroethylene (PTFE) or the like, that is heat-resistant and slippery. The abutment portion 32 protrudes toward the blade 25. The abutment portion 32 is of an arch-shaped cross section and is capable of abutting against a crest 25A of the blade 25. Each of the electrodes 33 is made of a general metal material such as copper or the like. Each of the electrodes 33 functions as one of bipolar electrodes for passing a high-frequency current through a biotissue. Each of the electrodes 33 is electrically connected to a high-frequency current supply circuit 41, to be described hereinafter, of the power supply unit 13 through an electric wire, i.e., one of first electric wires, extending through the second tubular portion 24.

The second treatment portion 23, i.e., a jaw, is angularly movably supported by a first pin 34 attached to the distal end of the tubular portion 21. The second treatment portion 23 is angularly movable about the first pin 34 for engagement with and disengagement from the treatment portion 22. The second treatment portion 23 has a second pin 35 coupled to the distal end of the second tubular portion 24. When the user grips the movable handle 18 and turns the movable handle 18 toward the fixed handle 17, the second tubular portion 24 moves back and forth with respect to the tubular portion 21. The force with which the second tubular portion 24 moves back and forth is transmitted through the second pin 35 to the second treatment portion 23, which is opened and closed with respect to the treatment portion 22.

The treatment portion 22 has a treatment portion body 36 made of a metal material, for example, a blade 25 that serves as a portion for contacting a biotissue, a heater 27 for heating the blade 25, and a thermally conductive member 26 disposed between the blade 25 and the heater 27 in contact therewith. The treatment portion body 36 serves as an outer shell of the treatment portion 22, and defines a rear surface 37 positioned on the side of the treatment portion 22 that is opposite the blade 25.

The blade 25 serves as a portion for coagulating and incising a biotissue with heat, and doubles as an electrode, i.e., the other of the bipolar electrodes, for passing a high-frequency current through a biotissue. The blade 25 is made of a metal material of good thermal conductivity and electric conductivity, such as copper, aluminum, or the like. The blade 25 is in the form of a slender plate that is of substantially the same length as the length of the treatment portion 22. The treatment portion body 36 may be integrally formed with the tubular portion 21. The blade 25 is electrically connected to the high-frequency current supply circuit 41, to be described hereinafter, of the power supply unit 13 through an electric wire, i.e., the other of the first electric wires, extending through the second tubular portion 24.

The heater 27 is constructed as a resistor, i.e., an electric heating wire, in the form of a metal foil deposited to a predetermined pattern, i.e., a pattern of straight lines and curved lines combined together, on a polyimide film as a base, for example. The metal foil should preferably be made of copper, stainless steel, or the like. The heater 27 together with the polyimide film is constructed as a sheet-like sheet heater. The heater 27 has a pair of terminals electrically connected to a heater driving circuit 42, to be described hereinafter, of the power supply unit 13 through a pair of electric wires, i.e., second electric wires, extending through the second tubular portion 24.

The thermally conductive member 26 has a length that is substantially the same as the length of the treatment portion 22, i.e., the blade 25, along the longitudinal directions L. Stated otherwise, the thermally conductive member 26 extends over the entire length of the blade 25 along the longitudinal directions L. The thermally conductive member 26 is in the form of a slender block that extends in directions along the longitudinal directions L. The thermally conductive member 26 has such thermal conductivity anisotropy that its thermal conductivity is higher in the longitudinal directions L of the blade 25 and its thermal conductivity is lower in the widthwise directions W that are transverse to the longitudinal directions L. Furthermore, the thermally conductive member 26 also has such thermal conductivity anisotropy that its thermal conductivity is higher in the plane directions of a plane that is transverse to the widthwise directions W and its thermal conductivity is lower in the widthwise directions W that are transverse to the longitudinal directions L.

As illustrated in FIG. 3, the thermally conductive member 26 is in the form of a block including a stack of sheets 43 that are made of a material containing carbon as a main component. Each of the sheets 43 extends in the plane directions of a plane that is transverse to the widthwise directions W of the blade 25. Although the sheets 43 should preferably be made of graphite, they may be sheets made of a material containing another carbon as a main component, e.g., carbon fiber, carbon nanotube, or the like. The thermally conductive member 26 can be formed as a block, i.e., can be made as a unitary body, by bonding the sheets 43 or sintering the sheets 43 while keeping them in abutment together. In the case where the sheets 43 are made of graphite, the thickness of each sheet 43 ranges from several to several hundreds μm, for example. In the case where the sheets 43 are made of graphite, the thermal conductivity of each sheet 43 in the plane directions thereof is of approximately 1500 W/mK, for example. The thermal conductivity of such a numerical value is much higher than the thermal conductivity of aluminum, for example, which is of approximately 200 W/mK that is known to have good thermal conductivity. In the case where the sheets 43 are made of graphite, the thermal conductivity of each sheet 43 in a direction transverse, or perpendicular, to the plane of the sheet 43 is in a range of approximately 5 to 10 W/mK, for example, that is approximately equivalent to the corresponding thermal conductivity of synthetic resin or the like.

As illustrated in FIG. 1, the power supply unit 13 has a controller 44. The controller 44 includes a printed circuit board and a central processing unit (CPU), a read-only memory (ROM), a random access memory (RAM), and a flash memory that are mounted on the printed circuit board. Functionally, the controller 44 has the heater driving circuit 42, the high-frequency current supply circuit 41, and a main control portion 45 for controlling the heater driving circuit 42 and the high-frequency current supply circuit 41. The main control portion 45 is able to control the supply of an electric current from the heater driving circuit 42 to the heater 27 and the supply of a high-frequency current from the high-frequency current supply circuit 41. When the surgeon operates the first switch 15A of the foot switch 15, the controller 44 controls the high-frequency current supply circuit 41 to supply a high-frequency current between the blade 25 and the electrode 33. When the surgeon operates the second switch 15B of the foot switch 15, the controller 44 controls the heater driving circuit 42 to supply an electric current to the heater 27, and also controls the high-frequency current supply circuit 41 to supply a high-frequency current between the blade 25 and the electrode 33. Providing the temperature of the heater 27 is uniform, the heater driving circuit 42 of the controller 44 controls the temperature of the heater 27 to be constant.

Operation of the treatment tool 11 according to the present embodiment will be described hereinafter. Prior to treating a biotissue as a treatment target using the treatment tool 11 according to the present embodiment, the surgeon keeps a path or port for accessing the treatment target, using a tubular guide, such as a cannula or the like, that can pierce a patient's skin or the like.

The surgeon can sandwich the biotissue as the treatment target between the treatment portion 22, i.e., the blade 25, and the second treatment portion 23, i.e., the abutment portion 32, in a treatment target region. Furthermore, the surgeon can apply high-frequency current energy to the biotissue sandwiched between the blade 25 and the electrode 33 by operating the first switch 15A that corresponds to the coagulation mode. The applied high-frequency current energy can coagulate the biotissue and seal a blood vessel. The surgeon can also apply thermal energy and high-frequency current energy to the biotissue by operating the second switch 15B that corresponds to the coagulation and incising mode. At this time, the temperature of the heater 27 rises to a high temperature of 200° C. or higher, for example.

The thermally conductive member 26 is of substantially the same length as the blade 25 along the longitudinal directions L. Each of the sheets 43 that make up the thermally conductive member 26 has a high thermal conductivity in the longitudinal directions L and the thicknesswise directions T that are the plane directions thereof. Therefore, the heat of the heater 27 spreads in the longitudinal directions L through the thermally conductive member 26, resulting in thermal equilibrium in the thermally conductive member 26 where the temperature is uniform along the longitudinal directions L therein. The heat that has uniformly spread in the longitudinal directions L is also transferred to the blade 25 via the thermally conductive member 26 that also has a high thermal conductivity in the thicknesswise directions T. The heat is thus uniformly transferred to the blade 25, making the blade 25 uniform in temperature. The temperature of the heater 27 that transfers the heat to the thermally conductive member 26 is kept uniform by the action of the thermally conductive member 26.

In the event that the heater 27 is suffering temperature variations, for example, when the controller 44 performs a control process for raising the temperature of the heater 27 in reference to the areas thereof where the temperature is lower, the areas of the heater 27 where the temperature is higher possibly tend to be overheated. The overheating may lead to damage of the heater 27. According to the present embodiment, since the temperature of the heater 27 is kept uniform, the heater 27 is prevented from being damaged by overheating. The treatment tool 11 thus has its reliability increased.

According to the present embodiment, while a biotissue and a blood vessel are being coagulated mainly by high-frequency current energy, the biotissue and the blood vessel are incised mainly by thermal energy transmitted to the blade 25 as described hereinbefore. In the coagulation and incising mode, therefore, the two types of energy, i.e., thermal energy and high-frequency current energy, are applied to efficiently treat, i.e., coagulate and incise, the sandwiched biotissue.

According to the first embodiment, the treatment tool 11 includes the blade 25 that contacts a biotissue, the heater 27, and the thermally conductive member 26 disposed between the blade 25 and the heater 27 in contact therewith. The thermally conductive member 26 has such thermal conductivity anisotropy that its thermal conductivity is higher in the longitudinal directions L of the blade 25 and its thermal conductivity is lower in the widthwise directions W that are transverse to the longitudinal directions L.

With this arrangement, the thermally conductive member 26 is capable of efficiently conducting heat in the longitudinal directions L of the blade 25 and of preventing heat from wastefully spreading in the widthwise directions W. The temperature of the blade 25 is thus uniformized in the longitudinal directions L thereof, thereby preventing difficulties such as coagulating and incising performance variations from occurring in different areas such as the distal-end side L1 and the proximal-end side L2 of the blade 25. The treatment tool 11 is thus capable of freely controlling the distribution of heat on the blade 25. In addition, the temperature of the heater 27 can be uniformized by the action of the thermally conductive member 26, preventing the heater 27 from being damaged by overheating and making the treatment tool 11 highly reliable.

The thermally conductive member 26 has such thermal conductivity anisotropy that its thermal conductivity is higher in the plane directions of a plane that is transverse to the widthwise directions W and its thermal conductivity is lower in the widthwise directions W that are transverse to the longitudinal directions L. With this arrangement, the thermal conductivity is rendered high in both the longitudinal directions L of the blade 25 and the thicknesswise directions T across the blade 25, the thermally conductive member 26, and the heater 27. The thermal conductivity is thus rendered high in not only the longitudinal directions L but also the thicknesswise directions T of the blade 25, making it possible to efficiently conduct heat from the heater 27 to the blade 25.

The thermally conductive member 26 includes a plurality of stacked sheets 43 extending in the plane directions of a plane that is transverse to the widthwise directions W. With this arrangement, the thermally conductive member 26 whose thermal conductivity is higher in the plane directions of a plane that is transverse to the widthwise directions W can be realized by a simple structure.

Each of the sheets 43 is made of a material containing carbon as a main component. With this arrangement, since the sheets 43 of the thermally conductive member 26 are made of a material containing carbon whose thermal conductivity is good, the heat of the heater 27 can efficiently be conducted in the longitudinal directions L and the thicknesswise directions T. The temperature of the blade 25 is thus uniformized to prevent different treating performances from taking place in different areas of the blade 25.

Each of the sheets 43 is made of graphite. With this arrangement, the sheets 43 of the thermally conductive member 26 are made of graphite that has an extremely good thermal conductivity and is less costly. Therefore, the treatment tool 11 whose treating performance is good and whose manufacturing cost is relatively low is realized.

Second Embodiment

Figure 4:
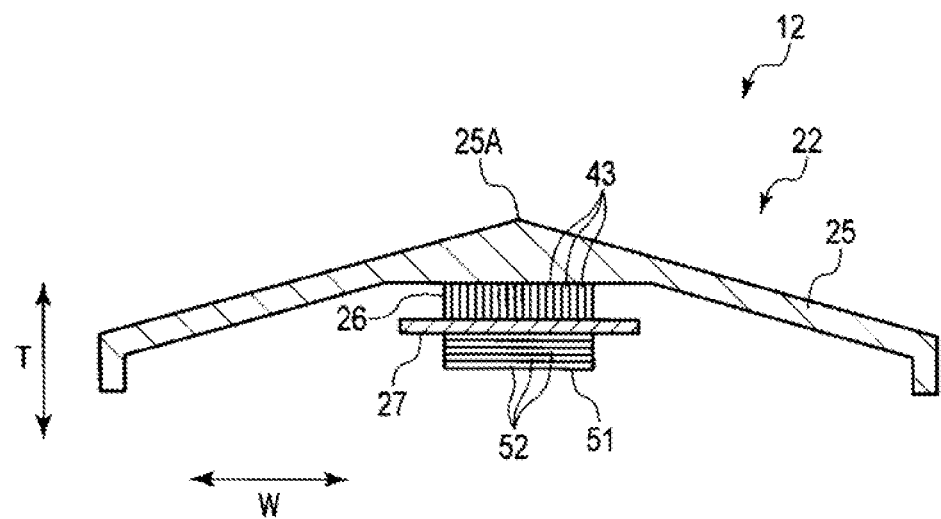
FIG. 4 is a cross-sectional view of a treatment tool according to a second embodiment, taken along a plane transverse to longitudinal directions of a treatment portion thereof.

A treatment tool 11 according to a second embodiment will be described hereinafter with reference to FIGS. 4 and 5. The treatment tool 11 according to the second embodiment is different from the first embodiment in that the treatment portion 22 includes a second thermally conductive member 51, but has other parts in common with the first embodiment. Hereinafter, those parts that are different from the first embodiment will mainly be described, and those parts that are in common with the first embodiment will not be illustrated or described.

The treatment portion 22 has a treatment portion body 36 (see FIG. 1) made of a metal material, for example, a blade 25 that serves as a portion for contacting a biotissue, a heater 27 for heating the blade 25, a thermally conductive member 26 disposed between the blade 25 and the heater 27, and a second thermally conductive member 51 disposed on the side of the heater 27 that is opposite its side facing the thermally conductive member 26, in contact with the heater 27.

The second thermally conductive member 51 is of substantially the same length as the treatment portion 22, i.e., the blade 25, along the longitudinal directions L. Stated otherwise, the second thermally conductive member 51 extends over the entire length of the blade 25 along the longitudinal directions L. The second thermally conductive member 51 is in the form of a slender block that extends in directions along the longitudinal directions L. The second thermally conductive member 51 has such thermal conductivity anisotropy that its thermal conductivity is higher in the longitudinal directions L of the blade 25 and its thermal conductivity is lower in the thicknesswise directions T across the blade 25, the thermally conductive member 26, and the heater 27. Furthermore, the second thermally conductive member 51 also has such thermal conductivity anisotropy that its thermal conductivity is higher in the plane directions of a plane that is transverse to the thicknesswise directions T and its thermal conductivity is lower in the thicknesswise directions T.

Figure 5:
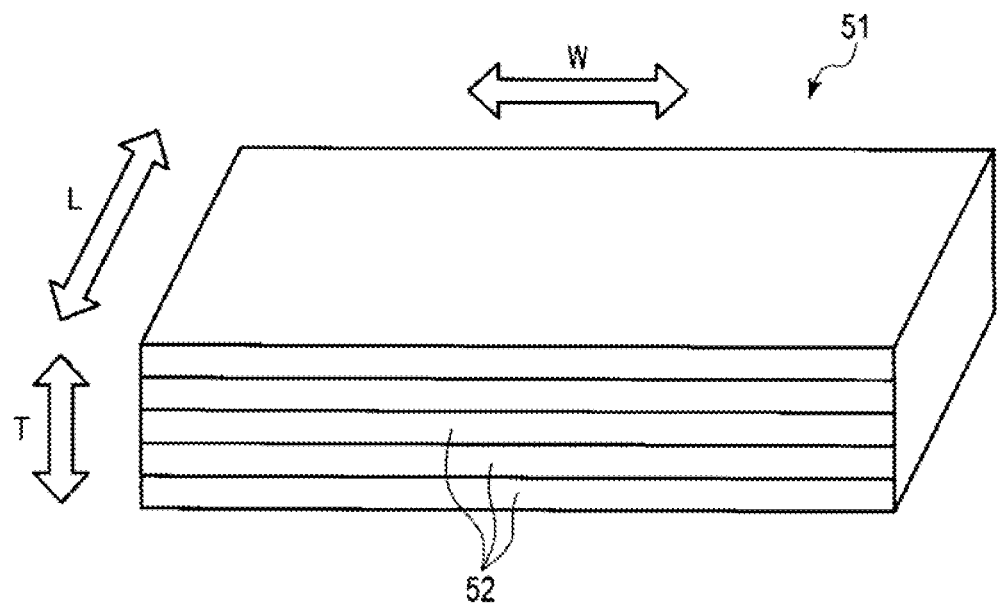
FIG. 5 is a perspective view of a second thermally conductive member illustrated in FIG. 4.

As illustrated in FIG. 5, the second thermally conductive member 51 is in the form of a block including a stack of second sheets 52 that are made of a material containing carbon as a main component. Each of the second sheets 52 extends in the plane directions of a plane that is transverse to the thicknesswise directions T. Although the second sheets 52 should preferably be made of graphite, they may be sheets made of a material containing another carbon as a main component, e.g., carbon fiber, carbon nanotube, or the like. In the case where the second sheets 52 are made of graphite, the thickness of each second sheet 52 ranges from several to several hundreds μm. In the case where the second sheets 52 are made of graphite, the thermal conductivity of each second sheet 52 in the plane directions thereof is of approximately 1500 W/mK, for example. The thermal conductivity of such a numerical value is much higher than the thermal conductivity of aluminum, for example, which is of approximately 200 W/mK, that is known to have good thermal conductivity. In the case where the second sheets 52 are made of graphite, the thermal conductivity of each second sheet 52 in a direction transverse, or perpendicular, to the plane of the second sheet 52 is in a range of approximately 5 to 10 W/mK, for example, that is approximately equivalent to the corresponding thermal conductivity of synthetic resin or the like. The second thermally conductive member 51 may be manufactured by a process that is similar to the process, referred to hereinbefore, of manufacturing the thermally conductive member 26.

Operation of the treatment tool 11 according to the present embodiment will be described hereinafter. As with the first embodiment, in the coagulation and incising mode, the thermally conductive member 26 conducts heat from the heater 27 uniformly to the blade 25, uniformizing the temperature of the blade 25 in the longitudinal directions L. The temperature of the heater 27 that conducts the heat to the thermally conductive member 26 is kept uniform in the longitudinal directions L by the action of the thermally conductive member 26.

The heat generated by the heater 27 is transmitted to the treatment portion body 36 disposed on the side opposite the blade 25. According to the present embodiment, the heat generated by the heater 27 can be conducted in the longitudinal directions L and the widthwise directions W of the treatment portion 22 by the second thermally conductive member 51 that is bonded to the side of the heater 27 that is opposite the blade 25. The heat thus spread in the longitudinal directions L and the widthwise directions W of the treatment portion 22 is returned to the heater 27 again, and is conducted via the thermally conductive member 26 to the blade 25. At this time, with respect to the thicknesswise directions T, since the thermal conductivity is kept low by the directions of the array of the second sheets 52 of the second thermally conductive member 51, the heat from the heater 27 is not positively guided to the treatment portion body 36 side, i.e., the rear surface 37 side, on the side opposite the blade 25. Consequently, the temperature of the treatment portion body 36, i.e., the rear surface 37, is prevented from rising.

According to the second embodiment, the treatment tool 11 includes the second thermally conductive member 51 disposed in contact with the side of the heater 27 that is opposite its side facing the thermally conductive member 26. The second thermally conductive member 51 has such thermal conductivity anisotropy that its thermal conductivity is higher in the longitudinal directions L and its thermal conductivity is lower in the thicknesswise directions T across the blade 25, the thermally conductive member 26, and the heater 27.

With this arrangement, heat can be conducted in a wide range with respect to the longitudinal directions L, and the heated conducted in the wide range can be returned to the heater 27 and utilized. Therefore, the treatment tool 11 is an energy saver where the heat generated by the heater 27 can efficiently be used. The treatment tool 11 is also capable of spreading the heat uniformly with respect to the longitudinal directions L for freely controlling a distribution of heat.

Furthermore as the second thermally conductive member 51 has its thermal conductivity lower in the thicknesswise direction T, the heat that has been transmitted to the second thermally conductive member 51 is not positively guided to the rear surface 37 side. Consequently, the treatment tool 11 prevents the temperature of the rear surface 37 side that is positioned opposite the blade 25 from rising, thus minimizing thermal invasion of a tissue around the treatment target region.

The second thermally conductive member 51 has such thermal conductivity anisotropy that its thermal conductivity is higher in the plane directions of a plane that is transverse to the thicknesswise directions T and its thermal conductivity is lower in the thicknesswise directions T.

With this arrangement, the thermal conductivity of the second thermally conductive member 51 is high in both the longitudinal directions L of the blade 25 and the widthwise directions W of the blade 25. The heat can thus be spread in the widthwise directions W of the blade 25, and can be returned to the heater 27 again. Accordingly, while the heat has been spread to a certain extent in the widthwise directions W by the second thermally conductive member 51, the heat can be conducted via the heater 27 and the thermally conductive member 26 to the blade 25. Thus, the heat can be conducted to the blade 25 while being spread to a certain extent in the widthwise directions W. Moreover, with the arrangement described hereinbefore, inasmuch as the thermal conductivity of the second thermally conductive member 51 is lower in the thicknesswise directions T, the temperature of the rear surface 37 side positioned opposite the blade 25 is prevented from rising.

The second thermally conductive member 51 includes a plurality of stacked second sheets 52 extending in the plane directions of a plane that is transverse to the thicknesswise directions T. With this arrangement, the second thermally conductive member 51 whose thermal conductivity is higher in the plane directions of a plane that is transverse to the thicknesswise directions T can be realized by a simple structure.

Each of the second sheets 52 is made of a material containing carbon as a main component. With this arrangement, since the second sheets 52 of the second thermally conductive member 51 are made of a material containing carbon whose thermal conductivity is good, the heat of the heater 27 can efficiently be conducted in the longitudinal directions L and the widthwise directions W. The temperature of the blade 25 is thus uniformized to prevent different treating performances from taking place in different areas of the blade 25.

The directions in which the second sheets 52 of the second thermally conductive member 51 extend are not limited to the plane directions of a plane that is transverse to the thicknesswise directions T. The directions in which the second sheets 52 of the second thermally conductive member 51 extend may be the plane directions of a plane that is transverse to the widthwise directions W of the blade 25, for example, as is the case with the directions in which the sheets 43 of the thermally conductive member 26 extend.

Modification of the Second Embodiment

A treatment tool according to a modification of the second embodiment will be described hereinafter with reference to FIGS. 6 and 7. The treatment tool 11 according to the modification of the second embodiment is different from the second embodiment as to the second thermally conductive member 51, but has other parts in common with the second embodiment. Hereinafter, those parts that are different from the second embodiment will mainly be described, and those parts that are in common with the second embodiment will not be illustrated or described.

The treatment portion 22 has a treatment portion body 36 (see FIG. 1) made of a metal material, for example, a blade 25 that serves as a portion for contacting a biotissue, a heater 27 for heating the blade 25, a thermally conductive member 26 disposed between the blade 25 and the heater 27, and a second thermally conductive member 51 disposed on the side of the heater 27 that is opposite its side facing the thermally conductive member 26, in contact with the heater 27.

The second thermally conductive member 51 is of substantially the same length as the blade 25 along the longitudinal directions L. Stated otherwise, the second thermally conductive member 51 extends over the entire length of the blade 25 along the longitudinal directions L. The second thermally conductive member 51 is in the form of a slender block that extends in directions along the longitudinal directions L. The second thermally conductive member 51 has such thermal conductivity anisotropy that (1) its thermal conductivity is higher in the longitudinal directions L of the blade 25 and (2) its thermal conductivity is higher in the thicknesswise directions T across the blade 25, the thermally conductive member 26, and the heater 27 and lower in a direction away from the heater 27.

Figure 6:
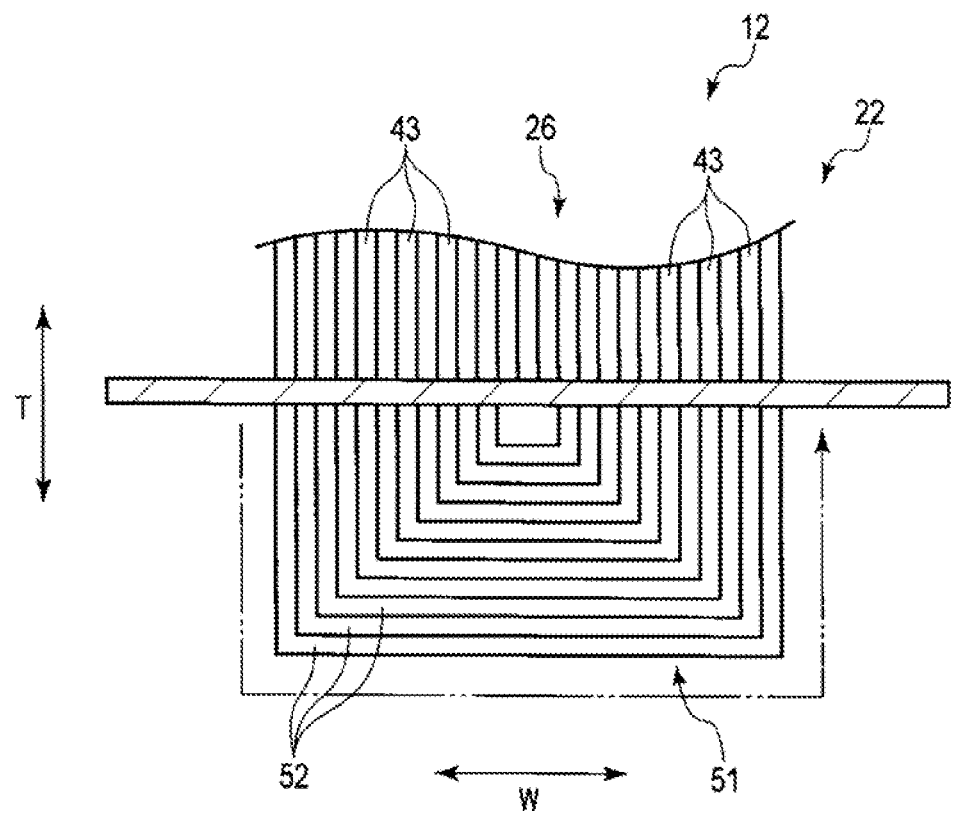
FIG. 6 is a cross-sectional view of a treatment tool according to a modification of the second embodiment, taken along a plane transverse to longitudinal directions thereof.

As illustrated in FIG. 6, the second thermally conductive member 51 is in the form of a block including a stack of second sheets 52 that are made of a material containing carbon as a main component. Each of the second sheets 52 extends in a U shape that is projected in a direction away from the heater 27. According to the present modification, therefore, the second sheets 52 has its thermal conductivity higher along the recessed surface of their U shape that is projected in the direction away from the heater 27. On the other hand, the second sheets 52 has its thermal conductivity lower in directions across the recessed surface of their U shape. The second thermally conductive member 51 has such thermal conductivity anisotropy.

Although the second sheets 52 should preferably be made of graphite, they may be sheets made of a material containing another carbon as a main component, e.g., carbon fiber, carbon nanotube, or the like. In the case where the second sheets 52 are made of graphite, the thickness of each second sheet 52 ranges from several to several hundreds μm. In the case where the second sheets 52 are made of graphite, the thermal conductivity of each second sheet 52 in the plane directions thereof is of approximately 1500 W/mK, for example. In the case where the second sheets 52 are made of graphite, the thermal conductivity of each second sheet 52 in a direction transverse, or perpendicular, to the plane of the second sheet 52 is in a range of approximately 5 to 10 W/mK, for example, that is approximately equivalent to the corresponding thermal conductivity of synthetic resin or the like.

Figure 7:
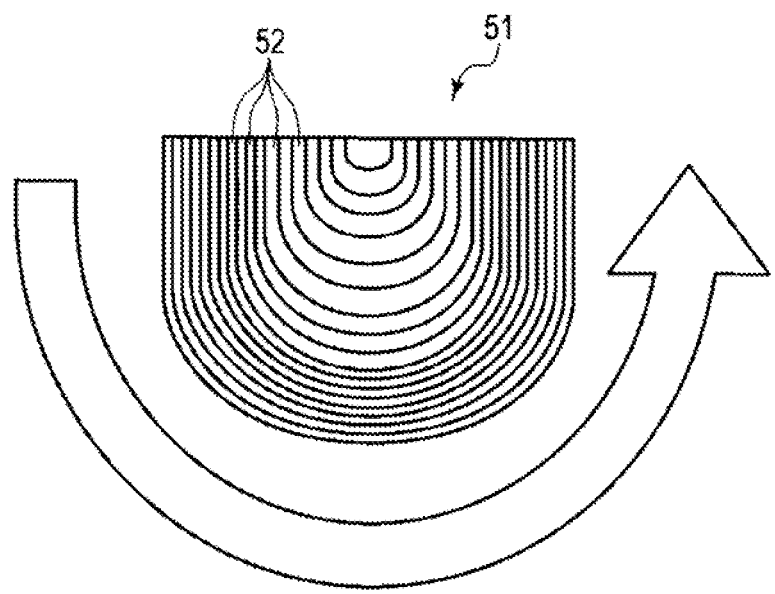
FIG. 7 is a schematic view schematically illustrating a process of manufacturing a second thermally conductive member illustrated in FIG. 6.

The second thermally conductive member 51 according to the present modification is formed as a block illustrated in FIG. 6 by, as illustrated in FIG. 7, stacking a plurality of second sheets 52 or graphite in thicknesswise directions, bending them into a U shape, and bonding or sintering the second sheets 52 together into a unitary body.

Operation of the treatment tool 11 according to the present modification will be described hereinafter. As with the first embodiment, in the coagulation and incising mode, the thermally conductive member 26 conducts heat from the heater 27 uniformly to the blade 25, uniformizing the temperature of the blade 25 in the longitudinal directions L. The temperature of the heater 27 that conducts the heat to the thermally conductive member 26 is kept uniform in the longitudinal directions L by the action of the thermally conductive member 26.

The heat generated by the heater 27 is also transmitted to the treatment portion body 36 side, i.e., the rear surface 37 side, opposite the blade 25. According to the present modification, the heat generated by the heater 27 can be conducted in the longitudinal directions L of the blade 25 by the second thermally conductive member 51 that is bonded to the side of the heater 27 that is opposite the blade 25. The heat thus spread in the longitudinal directions L of the blade 25 is returned to the heater 27 again, and is conducted via the thermally conductive member 26 to the blade 25. On the other hand, the heat emitted from the heater 27 and directed toward the rear surface 37 side, not in the longitudinal directions L, is directed toward the rear surface 37 side and then returned to the heater 27 through a U-shaped route as indicated by the dot-and-dash-line in FIG. 6 due to the thermal conductivity anisotropy of the second thermally conductive member 51. The heat returned to the heater 27 through such a route is transferred via the thermally conductive member 26 to the blade 25. Therefore, the heat emitted from the heater 27 and directed toward the rear surface 37 side is not directly transferred to the rear surface 37 side. As a result, the thermal conductivity is kept low in a direction away from the heater 27.

According to the present modification, since the second thermally conductive member 51 is designed such that the second sheets 52 are stacked in a U-shaped structure with respect to the thicknesswise directions T, making the thermal conductivity lower in the direction away from the heater 27. Therefore, the heat from the heater 27 is not positively guided to the treatment portion body 36 side, i.e., the rear surface 37 side, that is opposite the blade 25. The temperature is thus prevented from rising on the treatment portion body 36 side, i.e., the rear surface 37 side.

According to the present modification, the treatment tool 11 includes the second thermally conductive member 51 that is disposed in contact with the side of the heater 27 opposite to its side facing the thermally conductive member 26 and that has such thermal conductivity anisotropy that (1) its thermal conductivity is higher in the longitudinal directions L of the blade 25 and (2) its thermal conductivity is higher in the direction toward the heater 27 and lower in the direction away from the heater 27 with respect to the thicknesswise directions T across the blade 25, the thermally conductive member 26, and the heater 27. With this arrangement, heat can be conducted in a wide range with respect to the longitudinal directions L, and the heated conducted in the wide range can be returned to the heater 27 and utilized. Therefore, the treatment tool 11 is an energy saver where the heat generated by the heater 27 can efficiently be used. Furthermore, because the second thermally conductive member 51 has its thermal conductivity higher in the direction toward the heater 27 and lower in the direction away from the heater 27 with respect to the thicknesswise directions T, the heat transmitted to the second thermally conductive member 51 is returned to the heater 27 and is not positively guided to the rear surface 37 side. Consequently, the treatment tool 11 prevents the temperature of the rear surface 37 side that is positioned opposite the blade 25 from rising, thus minimizing thermal invasion of a tissue around the treatment target region.

The second thermally conductive member 51 has such thermal conductivity anisotropy that its thermal conductivity is higher along the recessed surface of its U shape that is projected in the direction away from the heater 27 and lower in directions across the recessed surface of its U shape. With this arrangement, the thermal conductivity of the second thermally conductive member 51 is rendered high in both the longitudinal directions L of the blade 25 and the directions along the recessed surface of its U shape that is projected in the direction away from the heater 27. The thermal conductivity thus made high not only spreads heat in the longitudinal directions L of the blade 25, but also returns heat directed in the direction away from the heater 27 on the rear surface 37 side opposite the blade 25 back to the heater 27 again. The heat thus spread makes the temperatures of the blade 25 and the heater 27 uniform with respect to the longitudinal directions L, and the heat directed toward the rear surface 37 side and returned to the heater 27 again is effectively used. The treatment tool 11 is an energy saver as the efficiency with which to use the heat is increased. With the arrangement described hereinbefore, furthermore, since the second thermally conductive member 51 is arranged to have its thermal conductivity lower in the directions across the recessed surface of its U shape, the temperature of the rear surface 37 side positioned opposite the blade 25 is prevented from rising.

The second thermally conductive member 51 includes a plurality of stacked second sheets 52 extending in the U shape that is projected in the direction away from the heater 27. With this arrangement, the second thermally conductive member 51 whose thermal conductivity is higher along the recessed surface of its U shape that is projected in the direction away from the heater 27 can be realized by a simple structure.

Third Embodiment

Figure 8:
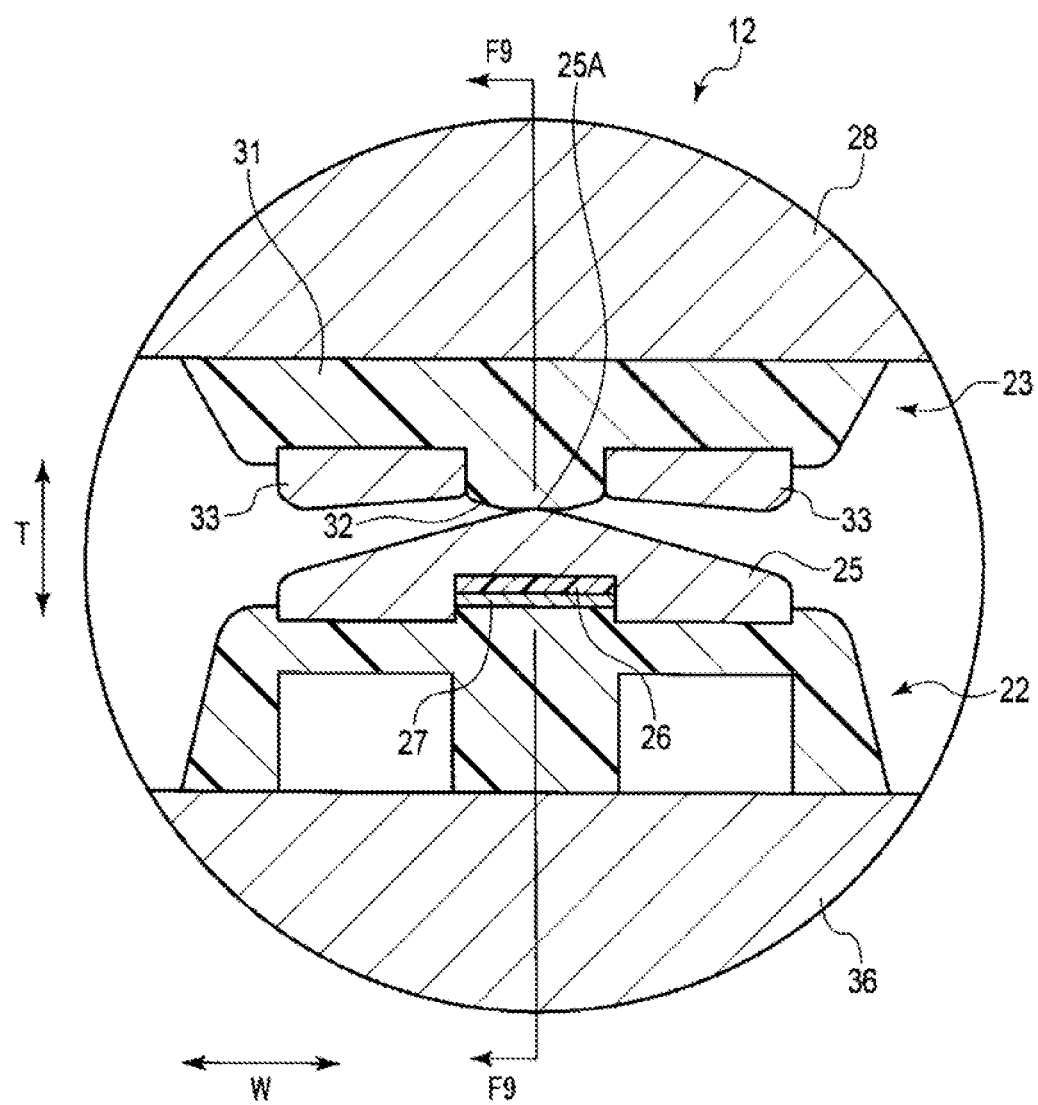
FIG. 8 is a cross-sectional view of a treatment tool according to a third embodiment, taken along a plane transverse to longitudinal directions thereof.
Figure 9:
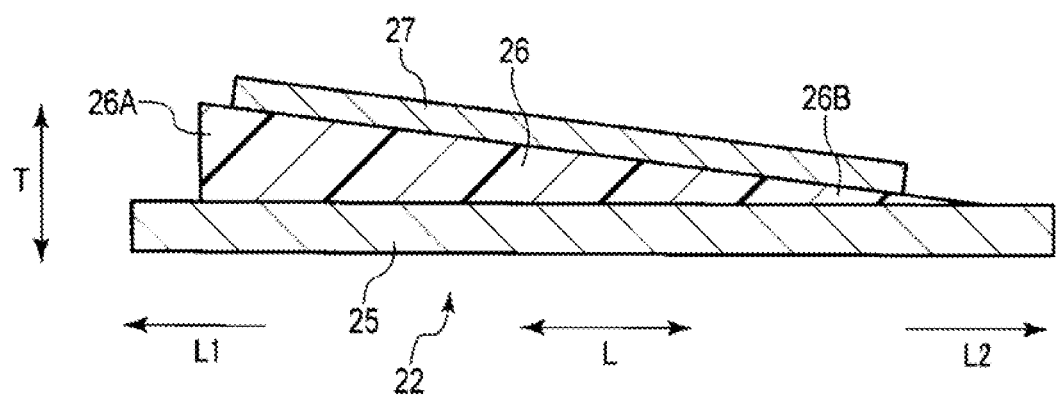
FIG. 9 is a cross-sectional view of the treatment tool illustrated in FIG. 8, taken along line F9-F9 thereof.
Figure 10:
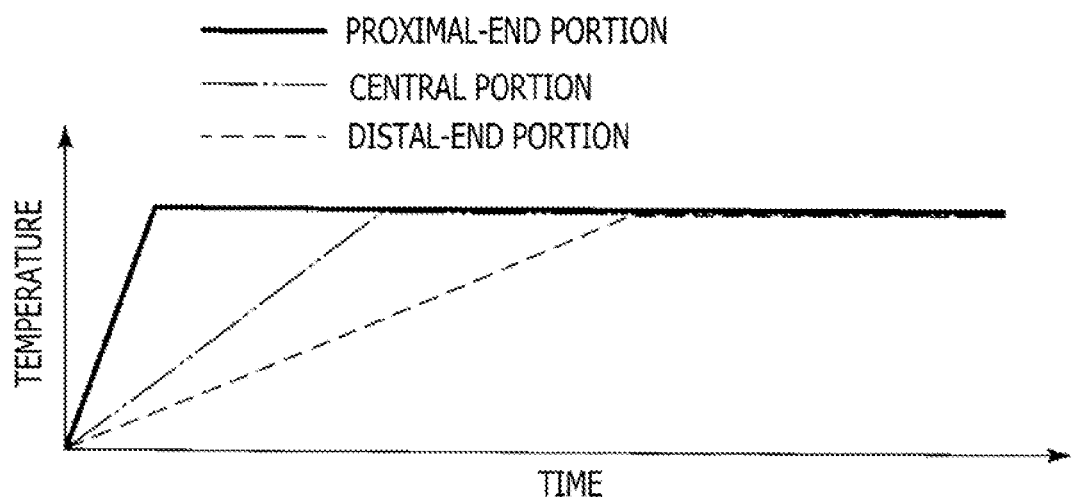
FIG. 10 is a graph illustrating temperature rises over time at a distal-end portion, a proximal-end portion, and a central portion of a blade of the treatment tool according to the third embodiment.

A treatment tool 11 according to a third embodiment will be described hereinafter with reference to FIGS. 8 through 10. The treatment tool 11 according to the third embodiment is different from the first embodiment as to the structure of the thermally conductive member 26 of the treatment portion 22, but has other parts in common with the first embodiment. Hereinafter, those parts that are different from the first embodiment will mainly be described, and those parts that are in common with the first embodiment will not be illustrated or described.

The treatment portion 22 has a treatment portion body 36 made of a metal material, for example, a blade 25 that serves as a portion for contacting a biotissue, a heater 27 for heating the blade 25, and a thermally conductive member 26 disposed between the blade 25 and the heater 27 in contact therewith. The blade 25 serves as a portion for coagulating and incising a biotissue with heat, and doubles as an electrode, i.e., the other of the bipolar electrodes, for passing a high-frequency current through a biotissue.

The thermally conductive member 26 extends over substantially the entire length of the blade 25 along the longitudinal directions L. The thermally conductive member 26 is in the form of a double-faced adhesive sheet that is thermally conductive and insulative. The thermally conductive member 26 as the double-faced adhesive sheet includes a base portion made of a synthetic resin material or the like. The thermally conductive member 26 has adhesive surfaces on its both surfaces, and the blade 25 and the heater 27 can be bonded thereto. The thermally conductive member 26 has a first portion 26A disposed on a distal-end side L1 in the longitudinal directions L and having a dimension in the thicknesswise directions T that increases toward the distal-end side L1, i.e., having a first thicknesswise dimension, and a second portion 26B disposed on a proximal-end side L2 in the longitudinal directions L and having a dimension in the thicknesswise directions T that decreases toward the proximal-end side L2, i.e., having a second thicknesswise dimension. Regarding the calculation of thermal conduction through a plane-parallel plate, it is known from the Fourier's law that a heat flux q is expressed by:

$$q = \lambda \cdot \Delta\theta / D \qquad \text{equation (1)}$$

This equation indicates that a quantity of heat flowing through a plate of 1 m$^2$ per second is proportional to the thermal conductivity $\lambda$ and the temperature difference $\Delta\theta$ between both surfaces and is in inverse proportion to the thickness D of the plate. Therefore, the quantity of heat that is conducted through the thermally conductive member 26 according to the present embodiment is smaller on the distal-end side L1 in the longitudinal directions L where the thickness is larger and is larger on the proximal-end side L2 in the longitudinal directions L where the thickness is smaller.

Operation of the treatment tool 11 according to the present embodiment will be described hereinafter. As with the first embodiment, in the coagulation and incising mode, the heat from the heater 27 is transferred via the thermally conductive member 26 to the blade 25. At this time, as illustrated in FIG. 10, in the longitudinal directions L, the proximal-end portion, i.e., the second portion 26B, of the blade 25 where the quality of heat conducted per unit time is larger reaches a temperature of approximately 200° C. as a target value quickly in a short time. On the other hand, in the longitudinal directions L, the distal-end portion, i.e., the first portion 26A, of the blade 25 where the quality of heat conducted per unit time is smaller reaches the temperature of approximately 200° C. as the target value slowly in a longer time than the time in which the proximal-end portion reaches the target value. An intermediate portion of the blade 25 in the longitudinal directions L reaches the temperature of approximately 200° C. as the target value in a time intermediate between the time in which the proximal-end portion reaches the target value and the time in which the distal-end portion reaches the target value.

As a result, when a biotissue is sandwiched between the abutment portion 32 of the second treatment portion 23 and the blade 25 of the treatment portion 22 and is coagulated or incised, the biotissue can be incised initially from the proximal-end side of the blade 25. On the other hand, the distal-end side of the blade 25 incises the biotissue at a timing later than the proximal-end side of the blade 25 starts to incise the biotissue. The intermediate portion of the blade 25 starts to incise the biotissue at an intermediate timing between the timing at which the proximal-end side of the blade 25 starts to incise the biotissue and the timing at which the distal-end side of the blade 25 starts to incise the biotissue. Consequently, an operational feeling that is attained when the treatment tool 11 according to the present embodiment incises the biotissue is similar to an operational feeling that is attained when scissors cut off an object.

According to the present embodiment, the treatment tool 11 includes the blade 25 for contacting a biotissue, the heater 27, and the thermally conductive member 26 disposed between the blade 25 and the heater 27 in contact therewith. The thermally conductive member 26 has the first portion 26A disposed on the distal-end side L1 in the longitudinal directions L of the blade 25, for conducting a prescribed quantity of heat per unit time from the heater 27 to the blade 25, and the second portion 26B disposed on the proximal-end side L2 in the longitudinal directions L, for conducting a quantity of heat, different from the prescribed quantity of heat described hereinbefore, per unit time from the heater 27 to the blade 25.

With this arrangement, there is a difference between the quantity of heat conducted per unit time by the first portion 26A on the distal-end side L1 in the longitudinal directions L and the quantity of heat conducted per unit time by the second portion 26B on the proximal-end side L2 in the longitudinal directions L. The quantities of heat supplied respectively to the first portion 26A and the second portion 26B can thus be freely controlled depending on the kind of the biotissue, i.e., an organ or a muscle, as the treatment target, and the manner in which the biotissue is treated. As a consequence, the treatment tool 11 is capable of freely controlling a distribution of heat depending on the biotissue as the treatment target and the manner in which the treatment target is treated, obtaining an ideal coagulating and incising performance.

The first portion 26A has the first thickness dimension in the thicknesswise directions T across the blade 25, the thermally conductive member 26, and the heater 27, and the second portion 26B has the second thickness dimension smaller than the first thickness dimension in the thicknesswise directions T. With this arrangement, a highly simple structure is realized for reducing the quantity of heat that passes through the first portion 26A per unit time and increasing the quantity of heat that passes through the second portion 26B per unit time. There is thus realized a treatment tool having an ideal coagulating and incising performance depending on the manner in which a treatment target is treated.

First Modification of the Third Embodiment

Figure 11:
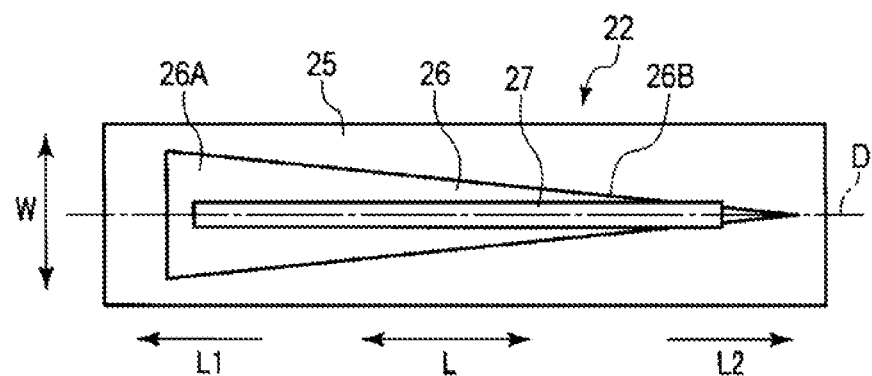
FIG. 11 is a plan view of a treatment tool according to a first modification of the third embodiment, as viewed from a heater side.

A treatment tool according to a first modification of the third embodiment will be described hereinafter with reference to FIG. 11. A treatment tool 11 according to the first modification is different from the third embodiment as to the structure of the thermally conductive member 26, but has other parts in common with the third embodiment. Hereinafter, those parts that are different from the third embodiment will mainly be described, and those parts that are in common with the third embodiment will not be illustrated or described.

The thermally conductive member 26 extends over substantially the entire length of the blade 25 along the longitudinal directions L. The thermally conductive member 26 is in the form of a double-faced adhesive sheet that is thermally conductive and insulative. Unlike the third embodiment, the thermally conductive member 26 has a substantially constant thickness throughout its entirety. The thermally conductive member 26 as the double-faced adhesive sheet includes a base portion made of a synthetic resin material or the like. The thermally conductive member 26 has adhesive surfaces on its both surfaces, and the blade 25 and the heater 27 can be bonded thereto. The thermally conductive member 26 has a first portion 26A disposed on a distal-end side L1 in the longitudinal directions L and having a dimension in the widthwise directions W that increases toward the distal-end side L1, i.e., having a first widthwise dimension, and a second portion 26B disposed on a proximal-end side L2 in the longitudinal directions L and having a dimension in the widthwise directions W that decreases toward the proximal-end side L2, i.e., having a second widthwise dimension.

Operation of the treatment tool 11 according to the present modification will be described hereinafter. The thermally conductive member 26 is of a reduced cross-sectional area on the proximal-end side L2 in the longitudinal directions L. Since the thermally conductive member 26 is narrower on the proximal-end side L2, heat concentrates on a central axis D of the blade 25. Therefore, even when the blade 25 on the proximal-end side repeatedly coagulates or incises a biotissue, the temperature of the blade 25 on the proximal-end side is less likely to drop. On the other hand, the thermally conductive member 26 is of an increased cross-sectional area, i.e., has an increased thermal load, on the distal-end side L1 in the longitudinal directions L. Therefore, the second portion 26B of the thermally conductive member 26 exists as a thermal load at all times on the distal-end side of the blade 25. Consequently, even when the controller 44 performs a control process for keeping the temperature constant in reference to the proximal-end side of the blade 25, i.e., the heater 27, the heater 27 is prevented from being damaged due to overheating caused on the distal-end side of the blade 25.

According to the present modification, the first portion 26A has the first widthwise dimension in the widthwise directions W transverse to the longitudinal directions L, and the second portion 26B has the second widthwise dimension that is smaller than the first widthwise dimension in the widthwise directions W. With this arrangement, a simple structure is realized for spreading heat in a wide range of the blade 25 on the wider distal-end side L1 and concentrating heat on the central axis D of the blade 25 on the narrower proximal-end side L2. As a consequence, the treatment tool 11 is capable of freely controlling a distribution of heat depending on a biotissue as a treatment target and the manner in which the treatment target is treated, obtaining an ideal coagulating and incising performance depending on the manner in which the biotissue is treated.

Second Modification of the Third Embodiment

Figure 12:
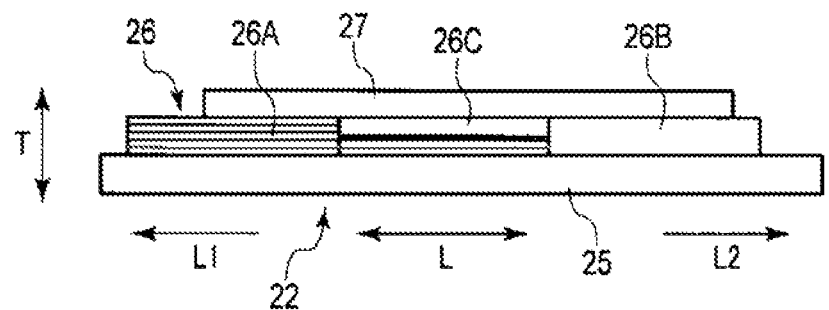
FIG. 12 is a side elevational view of a treatment tool according to a second modification of the third embodiment, as viewed from a lateral side.
Figure 13:
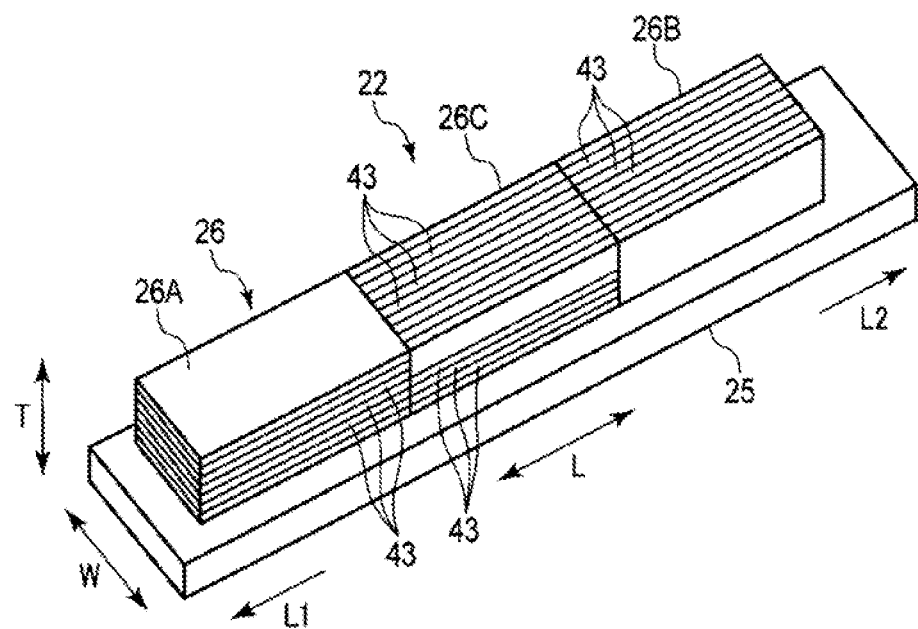
FIG. 13 is a perspective view of a thermally conductive member and a blade illustrated in FIG. 12.

A treatment tool 11 according to a second modification of the third embodiment will be described hereinafter with reference to FIGS. 12 and 13. The treatment tool 11 according to the second modification is different from the third embodiment as to the structure of the thermally conductive member 26, but has other parts in common with the third embodiment. Hereinafter, those parts that are different from the third embodiment will mainly be described, and those parts that are in common with the third embodiment will not be illustrated or described.

The thermally conductive member 26 extends over substantially the entire length of the blade 25 along the longitudinal directions L. The thermally conductive member 26 is in the form of a slender block that extends in directions along the longitudinal directions L. The thermally conductive member 26 has a first portion 26A positioned on a distal-end side L1 in the longitudinal directions L, a second portion 26B positioned on a proximal-end side L2 in the longitudinal directions L, and a third portion 26C positioned between the first portion 26A and the second portion 26B. The first through third portions 26A through 26C of the thermally conductive member 26 are in the form of blocks each including a stack of sheets 43 made of a material that contains carbon as a main component. Each of the sheets 43 of the first portion 26A extends in the plane directions of a plane transverse to the thicknesswise directions T of the blade 25, for example. Each of the sheets 43 of the second portion 26B extends in the plane directions of a plane transverse to the widthwise directions W of the blade 25, for example. The third portion 26C is a combination of a portion including sheets 43 that extend in the directions similar to those of the sheets 43 of the first portion 26A and a portion including sheets 43 that extend in the directions similar to those of the sheets 43 of the second portion 26B. The first through third portions 26A through 26C of the thermally conductive member 26 may be manufactured by a process that is the same as the process of manufacturing the thermally conductive member 26 according to the first embodiment.

Although the sheets 43 included in the first through third portions 26A through 26C should preferably be made of graphite, they may be sheets made of a material containing another carbon as a main component, e.g., carbon fiber, carbon nanotube, or the like.

The first through third portions 26A through 26C have such thermal conductivity anisotropy that their thermal conductivity is higher in the plane directions of the sheets 43 and lower in directions across the sheets 43. Therefore, the thermal conductivity of the first portion 26A is lower in the thicknesswise directions T. The thermal conductivity of the second portion 26B is higher in the thicknesswise directions T. The third portion 26C has a property intermediate between the first portion 26A and the second portion 26B.

Operation of the treatment tool 11 according to the present embodiment will be described hereinafter. As with the first embodiment, in the coagulation and incising mode, the heat from the heater 27 is transferred via the thermally conductive member 26 to the blade 25. At this time, in the first portion 26A of the thermally conductive member 26, the amount of heat conducted per unit time is smaller in proportion to its thermal conductivity. In the second portion 26B of the thermally conductive member 26, on the other hand, the amount of heat conducted per unit time is larger than the first portion 26A in proportion to its thermal conductivity. In the second portion 26B of the thermally conductive member 26, furthermore, heat is not wastefully spread in the widthwise directions W of the blade 25. In the third portion 26C of the thermally conductive member 26, the amount of conducted heat is of an intermediate value between the amount of conducted heat in the first portion 26A and the amount of conducted heat in the second portion 26B.

As a result, when a biotissue is sandwiched between the abutment portion 32 of the second treatment portion 23 and the blade 25 of the treatment portion 22 on the proximal-end side in the longitudinal directions L and is coagulated or incised, the temperature of the blade 25 on the proximal-end side is less likely to drop. The blade 25 on the proximal-end side is thus capable of performing a treatment for coagulating or incising a biotissue frequently. The temperature of the blade 25 rises slower on the distal-end side in the longitudinal directions L than on the proximal-end side, which means that the first portion 26A of the thermally conductive member 26 exists as a thermal load at all times. With this structure, in the absence of a biotissue, the temperature of the heater 27 is prevented from continuously rising, i.e., the heater 27 is prevented from producing idle heat and from being overheated. Therefore, even when the controller 44 performs a control process for keeping the temperature constant in reference to the proximal-end side of the blade 25, i.e., the heater 27, the heater 27 is prevented from being damaged due to overheating caused on the distal-end side of the blade 25.

According to the present modification, the first portion 26A includes a plurality of stacked graphite sheets extending in the plane directions of a plane transverse to the thicknesswise directions T across the blade 25, the thermally conductive member 26, and the heater 27, and the second portion 26B includes a plurality of stacked graphite sheets extending in the plane directions of a plane transverse to the widthwise directions W transverse to the longitudinal directions L. With this arrangement, a simple structure is realized for reducing the quantity of heat that passes through the first portion 26A per unit time and increasing the quantity of heat that passes through the second portion 26B per unit time. As a consequence, there is realized a treatment tool capable of obtaining an ideal coagulating and incising performance depending on the manner in which a treatment target is treated.

Fourth Embodiment

Figure 14:
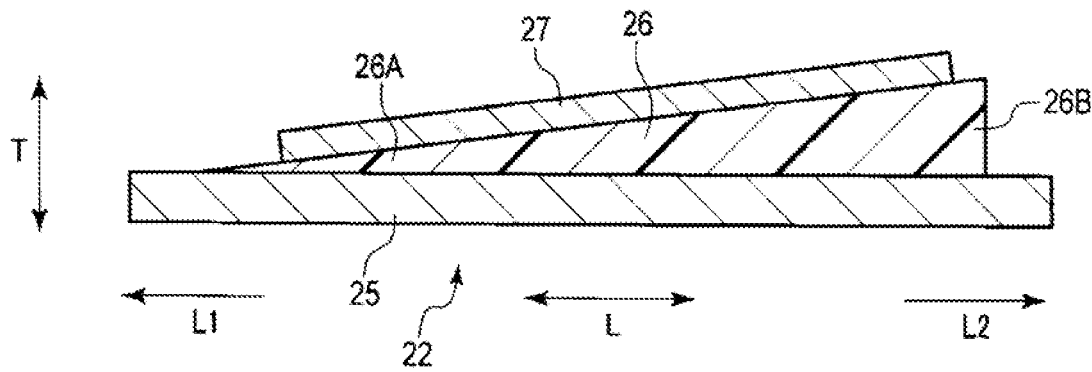
FIG. 14 is a cross-sectional view of a treatment tool according to a fourth embodiment, taken along a plane transverse to widthwise directions thereof.

A treatment tool according to a fourth embodiment will be described hereinafter with reference to FIG. 14. The treatment tool according to the fourth embodiment is different from the first embodiment as to the structure of the thermally conductive member 26, but has other parts in common with the first embodiment. Hereinafter, those parts that are different from the first embodiment will mainly be described, and those parts that are in common with the first embodiment will not be illustrated or described.

The treatment portion 22 has a treatment portion body 36 made of a metal material, for example, a blade 25 that serves as a portion for contacting a biotissue, a heater 27 for heating the blade 25, and a thermally conductive member 26 disposed between the blade 25 and the heater 27 in contact therewith. The blade 25 serves as a portion for coagulating and incising a biotissue with heat, and doubles as an electrode, i.e., the other of the bipolar electrodes, for passing a high-frequency current through a biotissue.

The thermally conductive member 26 extends over substantially the entire length of the blade 25 along the longitudinal directions L. The thermally conductive member 26 is in the form of a double-faced adhesive sheet that is thermally conductive and insulative. The thermally conductive member 26 as the double-faced adhesive sheet includes a base portion made of a synthetic resin material or the like. The thermally conductive member 26 has adhesive surfaces on its both surfaces, and the blade 25 and the heater 27 can be bonded thereto. The thermally conductive member 26 has a first portion 26A disposed on a distal-end side L1 in the longitudinal directions L and having a dimension in the thicknesswise directions T that decreases toward the distal-end side L1, i.e., having a first thicknesswise dimension, and a second portion 26B disposed on a proximal-end side L2 in the longitudinal directions L and having a dimension in the thicknesswise directions T that increases toward the proximal-end side L2, i.e., having a second thicknesswise dimension. Therefore, the quantity of heat that is conducted through the thermally conductive member 26 according to the present embodiment per unit time is larger on the distal-end side L1 in the longitudinal directions L where the thickness is smaller and is smaller on the proximal-end side L2 in the longitudinal directions L where the thickness is larger, according to the equation (1) described hereinbefore.

Operation of the treatment tool 11 according to the present embodiment will be described hereinafter. As with the first embodiment, in the coagulation and incising mode, the heat from the heater 27 is transferred via the thermally conductive member 26 to the blade 25. At this time, in the longitudinal directions L, distal-end portion, i.e., the first portion 26A, of the blade 25 where the quality of heat conducted per unit time is larger reaches a temperature of approximately 200° C. as a target value quickly in a short time. On the other hand, in the longitudinal directions L, the proximal-end portion, i.e., the second portion 26B, of the blade 25 where the quality of heat conducted per unit time is smaller reaches the temperature of approximately 200° C. as the target value slowly in a longer time than the time in which the distal-end portion reaches the target value. Stated otherwise, the thermally conductive member 26 as a thermal load connected to the heater 27 has a larger volume at the proximal-end portion. An intermediate portion of the blade 25 in the longitudinal directions L reaches the temperature of approximately 200° C. as the target value in a time intermediate between the time in which the proximal-end portion reaches the target value and the time in which the distal-end portion reaches the target value.

As a result, when a biotissue is sandwiched between the abutment portion 32 of the second treatment portion 23 and the blade 25 of the treatment portion 22 on the proximal-end side in the longitudinal directions L and is coagulated or incised, the temperature of the blade 25 on the distal-end side is less likely to drop. The blade 25 on the distal-end side is thus capable of performing a treatment for coagulating or incising a biotissue frequently. The temperature of the blade 25 rises slower on the proximal-end side in the longitudinal directions L than on the distal-end side. This means that the second portion 26B of the thermally conductive member 26 exists as a thermal load at all times on the proximal-end side of the blade 25. With this structure, in the absence of a biotissue, the temperature of the heater 27 is prevented from continuously rising, i.e., the heater 27 is prevented from producing idle heat and from being overheated. Consequently, even when the controller 44 performs a control process for keeping the temperature constant in reference to the distal-end side of the blade 25, i.e., the heater 27, the heater 27 is prevented from being damaged due to overheating caused on the proximal-end side of the blade 25.

According to the present embodiment, the first portion 26A has the first widthwise dimension in the thicknesswise directions T across the blade 25, the thermally conductive member 26, and the heater 27, and the second portion 26B has the second widthwise dimension that is larger than the first widthwise dimension in the thicknesswise directions T. With this arrangement, a highly simple structure is realized for increasing the quantity of heat that passes through the first portion 26A per unit time to make it possible to perform a treatment for incising and coagulating a treatment target with the distal end of the blade 25, and for increasing the thermal load on the proximal-end side of the heater 27 to prevent the proximal-end side of the heater 27 from being damaged due to overheating. As a consequence, the treatment tool 11 is capable of freely controlling a distribution of heat depending on the manner in which a treatment target is treated, obtaining an ideal coagulating and incising performance. Furthermore, a wider choice is available of materials for the heater 27, resulting in a cost reduction.

First Modification of the Fourth Embodiment

Figure 15:
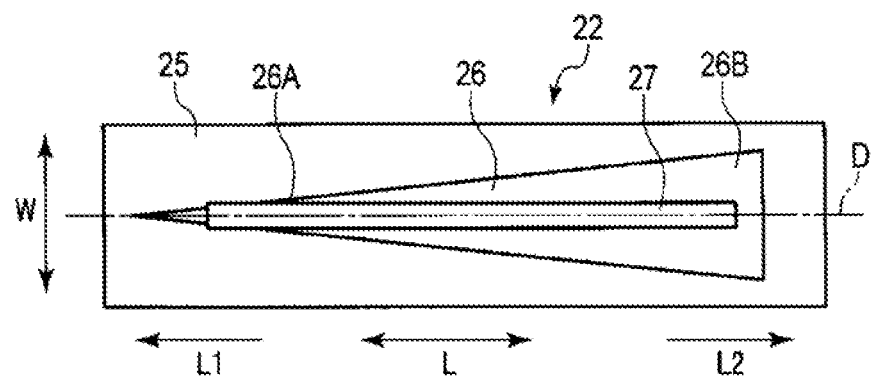
FIG. 15 is a plan view of a treatment tool according to a first modification of the fourth embodiment, as viewed from a heater side.

A treatment tool according to a first modification of the fourth embodiment will be described hereinafter with reference to FIG. 15. A treatment tool 11 according to the first modification is different from the fourth embodiment as to the structure of the thermally conductive member 26, but has other parts in common with the fourth embodiment. Hereinafter, those parts that are different from the fourth embodiment will mainly be described, and those parts that are in common with the fourth embodiment will not be illustrated or described.

The thermally conductive member 26 extends over substantially the entire length of the blade 25 along the longitudinal directions L. The thermally conductive member 26 is in the form of a double-faced adhesive sheet that is thermally conductive and insulative. Unlike the fourth embodiment, the thermally conductive member 26 has a substantially constant thickness throughout its entirety. Therefore, the thermally conductive member 26 can be machined with ease, and can be bonded to the heater 27 and the blade 25 with ease, resulting in a reduction in manufacturing cost.

The thermally conductive member 26 as the double-faced adhesive sheet includes a base portion made of a synthetic resin material or the like. The thermally conductive member 26 has adhesive surfaces on its both surfaces, and the blade 25 and the heater 27 can be bonded thereto. The thermally conductive member 26 has a first portion 26A disposed on a distal-end side L1 in the longitudinal directions L and having a dimension in the widthwise directions W that decreases toward the distal-end side L1, i.e., having a first widthwise dimension or having a smaller thermal load, and a second portion 26B disposed on a proximal-end side L2 in the longitudinal directions L and having a dimension in the widthwise directions W that increases toward the proximal-end side L2, i.e., having a second widthwise dimension or having a larger thermal load.

Operation of the treatment tool 11 according to the present modification will be described hereinafter. The thermally conductive member 26 is of a reduced cross-sectional area on the distal-end side L1 in the longitudinal directions L. Since the thermally conductive member 26 is narrower on the distal-end side L1, heat concentrates on a central axis D of the blade 25. Therefore, even when the blade 25 on the distal-end side repeatedly coagulates or incises a biotissue, the temperature of the blade 25 on the distal-end side is less likely to drop. On the other hand, the thermally conductive member 26 is of an increased cross-sectional area on the proximal-end side L2 in the longitudinal directions L. Therefore, the second portion 26B of the thermally conductive member 26 exists as a thermal load at all times on the proximal-end side of the blade 25. Consequently, even when the controller 44 performs a control process for keeping the temperature constant in reference to the distal-end side of the blade 25, i.e., the heater 27, the heater 27 is prevented from being damaged due to overheating caused on the proximal-end side of the blade 25. Consequently, the present modification operates in the same manner as the fourth embodiment described hereinbefore.

According to the present modification, the first portion 26A has the first widthwise dimension in the widthwise directions W transverse to the longitudinal directions L, and the second portion 26B has the second widthwise dimension that is smaller than the first widthwise dimension in the widthwise directions W. With this arrangement, a simple structure is realized for concentrating heat on the central axis D of the blade 25 on the narrower distal-end side L1 to make it possible to perform a treatment for repeatedly incising and coagulating a treatment target at the distal end of the blade 25, and for increasing a thermal load on the proximal-end side of the heater 27 to prevent the proximal-end side of the heater 27 from being damaged due to overheating. As a consequence, the treatment tool 11 is capable of freely controlling a distribution of heat depending on the manner in which biotissue as a treatment target is treated, obtaining an ideal coagulating and incising performance depending on the manner in which the biotissue is treated.

Second Modification of the Fourth Embodiment

Figure 16:
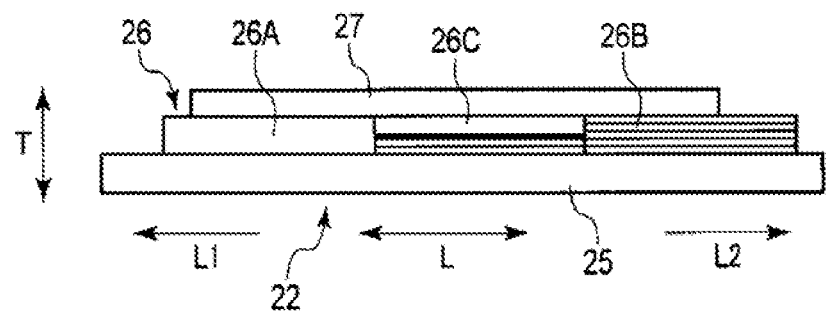
FIG. 16 is a side elevational view of a treatment tool according to a second modification of the fourth embodiment, as viewed from a lateral side.
Figure 17:
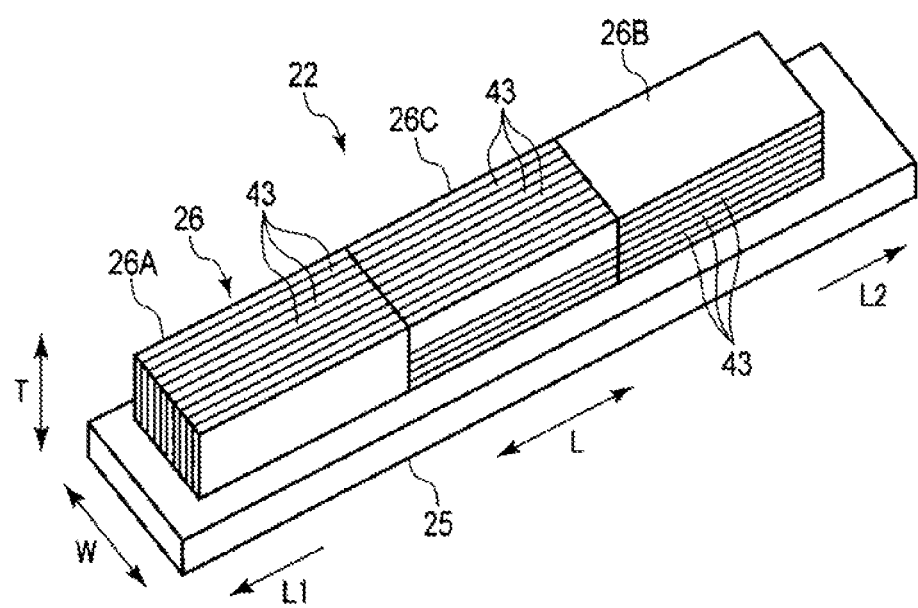
FIG. 17 is a perspective view of a thermally conductive member and a blade illustrated in FIG. 16.

A treatment tool according to a second modification of the fourth embodiment will be described hereinafter with reference to FIGS. 16 and 17. A treatment tool 11 according to the second modification is different from the fourth embodiment as to the structure of the thermally conductive member 26, but has other parts in common with the fourth embodiment. Hereinafter, those parts that are different from the fourth embodiment will mainly be described, and those parts that are in common with the fourth embodiment will not be illustrated or described.

The thermally conductive member 26 extends over substantially the entire length of the blade 25 along the longitudinal directions L. The thermally conductive member 26 is in the form of a slender block that extends in directions along the longitudinal directions L. The thermally conductive member 26 has a first portion 26A positioned on a distal-end side L1 in the longitudinal directions L, a second portion 26B positioned on a proximal-end side L2 in the longitudinal directions L, and a third portion 26C positioned between the first portion 26A and the second portion 26B. The first through third portions 26A through 26C of the thermally conductive member 26 are in the form of blocks each including a stack of sheets 43 made of a material that contains carbon as a main component. Each of the sheets 43 of the first portion 26A extends in the plane directions of a plane transverse to the widthwise directions W of the blade 25, for example. Each of the sheets 43 of the second portion 26B extends in the plane directions of a plane transverse to the thicknesswise directions T of the blade 25, for example. The third portion 26C is a combination of a portion including sheets 43 that extend in the directions similar to those of the sheets 43 of the first portion 26A and a portion including sheets 43 that extend in the directions similar to those of the sheets 43 of the second portion 26B. The first through third portions 26A through 26C of the thermally conductive member 26 may be manufactured by a process that is the same as the process of manufacturing the thermally conductive member 26 according to the first embodiment.

Although the sheets 43 included in the first through third portions 26A through 26C should preferably be made of graphite, they may be sheets made of a material containing another carbon as a main component, e.g., carbon fiber, carbon nanotube, or the like. The first through third portions 26A through 26C of the thermally conductive member 26 can be formed as a block by bonding the sheets 43 or sintering the sheets 43 while keeping them in abutment together.

The first through third portions 26A through 26C have such thermal conductivity anisotropy that their thermal conductivity is higher in the plane directions of the sheets 43 and lower in directions across the sheets 43. Therefore, the thermal conductivity of the first portion 26A is higher in the thicknesswise directions T. The thermal conductivity of the second portion 26B is lower in the thicknesswise directions T. The third portion 26C has a property intermediate between the first portion 26A and the second portion 26B.

Operation of the treatment tool 11 according to the present embodiment will be described hereinafter. As with the first embodiment, in the coagulation and incising mode, the heat from the heater 27 is transferred via the thermally conductive member 26 to the blade 25. At this time, in the first portion 26A of the thermally conductive member 26, the amount of heat conducted per unit time is larger in proportion to its thermal conductivity. In the first portion 26A of the thermally conductive member 26, furthermore, heat is not wastefully spread in the widthwise directions W of the blade 25. In the second portion 26B of the thermally conductive member 26, on the other hand, the amount of heat conducted per unit time is smaller than the first portion 26A in proportion to its thermal conductivity. In the third portion 26C of the thermally conductive member 26, the amount of conducted heat is of an intermediate value between the amount of conducted heat in the first portion 26A and the amount of conducted heat in the second portion 26B.

As a result, when a biotissue is sandwiched between the abutment portion 32 of the second treatment portion 23 and the blade 25 of the treatment portion 22 on the proximal-end side in the longitudinal directions L and is coagulated or incised, the temperature of the blade 25 on the distal-end side is less likely to drop. The blade 25 on the distal-end side is thus capable of performing a treatment for coagulating or incising a biotissue frequently. The temperature of the blade 25 rises slower on the proximal-end side in the longitudinal directions L than on the distal-end side, which means that the second portion 26B of the thermally conductive member 26 exists as a thermal load at all times. With this structure, in the absence of a biotissue, the temperature of the heater 27 is prevented from continuously rising, i.e., the heater 27 is prevented from producing idle heat and from being overheated. Therefore, even when the controller 44 performs a control process for keeping the temperature constant in reference to the distal-end side of the blade 25, i.e., the heater 27, the heater 27 is prevented from being damaged due to overheating caused on the proximal-end side of the blade 25.

According to the present modification, the first portion 26A includes a plurality of stacked graphite sheets extending in the plane directions of a plane transverse to the widthwise directions W transverse to the longitudinal directions L, and the second portion 26B includes a plurality of stacked graphite sheets extending in the plane directions of a plane transverse to the thicknesswise directions T across the blade 25, the thermally conductive member 26, and the heater 27. With this arrangement, a simple structure is realized for performing a treatment for repeatedly incising and coagulating a treatment target at the distal end of the blade 25, and for increasing a thermal load on the proximal-end side of the heater 27 to prevent the proximal-end side of the heater 27 from being damaged due to overheating. As a consequence, the treatment tool 11 is capable of obtaining an ideal coagulating and incising performance depending on the manner in which a treatment target is treated.

The disclosed technology is not limited to the embodiments described hereinbefore, but changes and modifications may be made therein without departing from the scope of the invention. Furthermore, the treatment tools according to the embodiments and the modifications described hereinbefore may be combined into a single treatment tool.

In sum, one aspect of the disclosed technology is directed to a treatment tool having a blade configured to engage with a treatment target. A heater is configured to be spaced apart from the blade. A first thermally conductive member is sandwiched between the blade and the heater so as to transmit heat to the blade. The first thermally conductive member includes a first thermal conductivity anisotropy that is higher in longitudinal directions of the blade and is lower in widthwise directions transverse to the longitudinal directions.

The first thermal conductivity anisotropy is higher in plane directions of a plane transverse to the widthwise directions and is lower in the widthwise directions. The first thermally conductive member is defined by a plurality of first stacked sheets extending in the plane directions of the plane transverse to the widthwise directions. Each of the plurality of sheets is substantially made of either carbon or graphite or combination thereof. Each of the sheets contains graphite. The treatment tool further comprises a second thermally conductive member attached to the heater opposite from the first thermally conductive member. The second thermally conductive member includes a second thermal conductivity anisotropy that is higher in the longitudinal directions and is lower in thicknesswise directions across the blade, the first thermally conductive member, and the heater. The second thermal conductivity anisotropy is higher in plane directions of a plane transverse to the thicknesswise directions and is lower in the thicknesswise directions. The second thermally conductive member is defined by a plurality of second stacked sheets extending in plane directions of a plane transverse to the widthwise directions. Each of the plurality of second stacked sheets is substantially made of carbon.

The treatment tool further includes a second thermally conductive member attached to the heater opposite from the first thermally conductive member. The second thermally conductive member includes a second thermal conductivity anisotropy that is higher in the longitudinal directions and in a direction toward the heater and is lower in a direction away from the heater with respect to thicknesswise directions across the blade, the second thermally conductive member, and the heater. The second thermal conductivity anisotropy is higher along a recessed surface of a U shape that is projected in the direction away from the heater and lower in a direction across the recessed surface of the U shape. The second thermally conductive member includes a plurality of second stacked sheets extending in a U shape that is projected in the direction away from the heater. The second stacked sheets is substantially made of carbon.

Another aspect of the disclosed technology is directed to a treatment tool having a blade configured to engage with a treatment target. A heater is configured to be spaced apart from the blade. A first thermally conductive member is sandwiched between the blade and the heater so as to transmit heat to the blade. The first thermally conductive member includes respective first and second portions each of which disposed on respective distal-end and proximal-end sides in longitudinal directions of the blade for thermally conducting a different prescribed quantity of heat per unit time from each of the respective first and second portions to the blade via the heater.

The first portion has a first thicknesswise dimension in thicknesswise directions across the blade, the thermally conductive member, and the heater. The second portion has a second thicknesswise dimension smaller or larger than the first thicknesswise dimension in the thicknesswise directions. The first portion has a first widthwise dimension in widthwise directions transverse to the longitudinal directions. The second portion has a second widthwise dimension larger or smaller than the first widthwise dimension in the widthwise directions. The first portion includes a plurality of first stacked graphite sheets extending in plane directions of a plane transverse to thicknesswise directions across the blade, the thermally conductive member, and the heater. The second portion includes a plurality of second stacked graphite sheets extending in plane directions of a plane transverse to widthwise directions transverse to the longitudinal directions. The first portion includes a plurality of first stacked graphite sheets extending in plane directions of a plane transverse to widthwise directions transverse to the longitudinal directions. The second portion includes a plurality of second stacked graphite sheets extending in plane directions of a plane transverse to thicknesswise directions across the blade, the thermally conductive member, and the heater. The treatment tool further includes an abutment portion facing the blade for abutting against the treatment target so as to sandwich the treatment target between the abutment portion and the blade. The treatment target is a biological tissue.

A further aspect of the disclosed technology is directed to a treatment tool having a blade configured to engage with a treatment target. A heater is configured to be spaced apart from the blade. A first thermally conductive member is sandwiched between the blade and the heater so as to transmit heat to the blade. The first thermally conductive member includes respective first and second portions each of which is disposed on respective distal-end and proximal-end sides in longitudinal directions of the blade for thermally conducting a different prescribed quantity of heat per unit time from each of the respective first and second portions to the blade via the heater. The first thermally conductive member includes a first thermal conductivity anisotropy that is higher in longitudinal directions of the blade and is lower in widthwise directions transverse to the longitudinal directions.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment tool comprising:
   a blade configured to engage with a treatment target;
   a heater spaced apart from the blade; and
   a first thermally conductive member sandwiched between the blade and the heater so as to transmit heat to the blade,
   wherein the first thermally conductive member includes a first thermal conductivity anisotropy such that a thermal conductivity of the first thermally conductive member is higher in longitudinal directions of the blade and is lower in widthwise directions of the blade that are transverse to the longitudinal directions.

2. The treatment tool of claim 1, wherein:
   the first thermal conductivity anisotropy is higher in plane directions of a plane transverse to the widthwise directions and is lower in the widthwise directions, and
   the first thermally conductive member is defined by a plurality of first stacked sheets extending in the plane directions of the plane transverse to the widthwise directions.

3. The treatment tool of claim 2, wherein:
   each of the plurality of sheets is substantially made of either carbon or graphite or a combination thereof, and each of the sheets contains graphite.

4. The treatment tool of claim 1, further comprising a second thermally conductive member being attached to the heater opposite from the first thermally conductive member, wherein the second thermally conductive member includes a second thermal conductivity anisotropy that is higher in the longitudinal directions and is lower in thicknesswise directions across the blade, the first thermally conductive member, and the heater.

5. The treatment tool of claim 4, wherein the second thermal conductivity anisotropy is higher in plane directions of a plane transverse to the thicknesswise directions and is lower in the thicknesswise directions.

6. The treatment tool of claim 5, wherein the second thermally conductive member is defined by a plurality of second stacked sheets extending in plane directions of a plane transverse to the widthwise directions.

7. The treatment tool of claim 6, wherein each of the plurality of second stacked sheets is substantially made of carbon.

8. The treatment tool of claim 1, further comprising
   a second thermally conductive member that is attached to the heater opposite from the first thermally conductive member, wherein the second thermally conductive member includes a second thermal conductivity anisotropy that is higher in the longitudinal directions and in a direction toward the heater and is lower in a direction away from the heater with respect to thicknesswise directions across the blade, the second thermally conductive member, and the heater.

9. The treatment tool of claim 8, wherein the second thermal conductivity anisotropy is higher along a recessed surface of a U shape that is projected in the direction away from the heater and lower in a direction across the recessed surface of the U shape.

10. The treatment tool of claim 9, wherein
    the second thermally conductive member includes a plurality of second stacked sheets extending in a U shape that is projected in the direction away from the heater; and
    the second stacked sheets is substantially made of carbon.

11. The treatment tool according to claim 1, wherein a width of the blade in the widthwise directions is larger than a width of the first thermally conductive member in the widthwise directions, and the widthwise directions are transverse to a stacking direction of the blade, the first thermally conductive member, and the heater.

12. The treatment tool according to claim 11, further comprising:
    a jaw configured to open and close with respect to the blade, the jaw including an electrode, wherein:
    a center part of the blade in the widthwise directions includes a crest such that in the widthwise directions towards the center part, the blade is inclined in a direction toward the jaw, and
    the blade and jaw are configured such that a high frequency current can flow between the blade and the electrode of the jaw.

* * * * *